United States Patent [19]
Nikodem

[11] Patent Number: 5,813,854
[45] Date of Patent: Sep. 29, 1998

[54] ORTHODONTIC BRACE INSTALLATION DEVICE

[76] Inventor: Stephen G. Nikodem, 4110 Von Talge, St. Louis, Mo. 63128

[21] Appl. No.: 834,954

[22] Filed: Apr. 7, 1997

[51] Int. Cl.[6] ...................................................... A61C 3/00
[52] U.S. Cl. .................................. 433/29; 433/3; 433/215
[58] Field of Search ................................ 433/3, 290, 215

[56] References Cited

U.S. PATENT DOCUMENTS

| | | | |
|---|---|---|---|
| 3,949,477 | 4/1976 | Cohen et al. | 433/3 |
| 4,952,143 | 8/1990 | Becker et al. | 433/215 |
| 5,316,473 | 5/1994 | Hare | 433/29 |

*Primary Examiner*—John J. Wilson

[57] ABSTRACT

A device (10) used in orthodontic processes in which light is supplied from a source (40) through a light transmissive cable (42) and directed at a patient's teeth (T). A housing (12) is deformable to conform to an arch shape of a set (SU, SL) of the patient's teeth. The length of the housing corresponds to the arcuate length of the set of teeth, and an adaptor (48) attaches the housing to an end (44) of the cable for light to be directed into the housing. A light diffusion system (18) diffuses the light throughout the housing which has a light transmissive surface (14) by which the diffused light is simultaneously directed at all of the patient's teeth on which the dental/orthodontic process is being pre-formed to substantially reduce the amount of time required for light to be used in performing the process.

21 Claims, 4 Drawing Sheets

ORTHODONTIC BRACE INSTALLATION DEVICE

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention relates to braces worn by people on their teeth, and more particularly, to a device for quickly and efficiently bonding braces to a patient's teeth in substantially less time than is now required using conventional orthodontic methods.

In orthodontic practice, the installation of braces to a person's teeth require that brackets be fitted to each tooth, the brackets supporting a wire used to conform the teeth to a desired arch so that, over time, the desired arch shape becomes permanent. The fitting process for the brackets involves chemical bonding of a bracket to a tooth. Bonding procedures currently depend heavily on the use of fiber optics for both precision and accuracy in placing brackets on the teeth. That is, each bracket is fitted onto a tooth using a light activated curing material. When a fiber optic cable is positioned by the orthodontist or a technician so light from a laser source, emitted from the end of the cable, is directed at a chemically masked portion of the tooth where the bracket is to placed, the resulting curing process permanently affixes the bracket to the tooth. Current practice requires an initial ten second per tooth application of light, and a subsequent sixty second (one minute) per tooth light application. Approximately twenty (20) teeth are usually fitted with braces, so the total time of light application is on the order of twenty-five minutes per patient. In some circumstances, this time period can be fifty minutes or more.

Another process in which an argon/$CO_2$ laser is used in dental/orthodontic practice is in the whitening of discolored teeth. The application time for light in this process is also extensive because of the amount of time light must be applied to each tooth. With either process, the time now required for a dentist/orthodontist to perform the procedure reduces the number of patients he or she can see and treat during any given period. Other dental procedures that might benefit from the above-mentioned device is cosmetic dental bonding (veneers), multiple sealant placement and multiple synthetic restorative procedures.

BRIEF SUMMARY OF THE INVENTION

Among the several objects of the present invention may be noted the provision of an orthodontic brace installation device and which can also be used in teeth whitening processes, as well as other dental procedures as mentioned above;

the provision of such a device by which the amount of time light must be applied to a patient's teeth to attach brackets to the teeth is significantly reduced;

the provision of such a device which is attaches to an existing fiber optic cable used to direct light at the patient's teeth to attach a bracket to a tooth, but which allows light to be simultaneously directed at all of the teeth in an upper or lower set of teeth to which braces are attached so that each tooth does not have to be individually treated as is now required;

the provision of such a device to be conformable to the arch shape of a person's set of teeth in order to efficiently direct light at all of the teeth at the same time;

the provision of such a device in which conformance of the device to the shape of a person's set of teeth can be done in advance of the person's treatment using a mold previously taken of the person's teeth thereby to further reduce treatment time;

the provision of such a device to come in a variety of sizes so to accommodate people having different sized sets of teeth;

the provision of such a device to use a soft, deformable material which is readily shaped to conform to the arch of a person's upper or lower set of teeth and to employ a light diffusion system by which light from the end of a fiber optic cable to which the device is attached is simultaneously diffused throughout the device and directed at all of the patient's teeth to which either braces are being applied, or which are being whitened or being restored;

the provision of such a device which is readily attached and detached from the fiber optic cable, for disposal and/or autoclavable purposes in conformance with infection control policies at the using site;

the provision of such a device which is relatively low in cost;

the provision of such a device which can reduce light application time now required by a dentist/orthodontist to affix brackets to teeth, whiten teeth, or restore teeth; and the provision of such a device which can be used with animals as well as humans.

In accordance with the invention, generally stated, a device used in performing orthodontic processes in which light supplied from a source through a light transmissive cable is directed at a patient's teeth comprises a housing deformable to conform to an arch shape of the patient's set of teeth. The length of the housing corresponds to the arcuate length of the set of teeth and the housing is attached to an end of the cable for light transmitted through the cable to be directed into the housing. The light is diffused throughout the housing, and the housing has a light transmissive surface by which diffused light is directed from the device simultaneously at all of the patient's teeth on which the orthodontic process is being performed. This substantially reduces the amount of time required for light to be used in performing the process. Other objects and features will be in part apparent and in part pointed out hereinafter.

BRIEF DESCRIPTION OF THE SEVERAL VIEWS OF THE DRAWINGS

In the drawings.

Corresponding reference characters indicate corresponding parts throughout the drawings.

DETAILED DESCRIPTION OF THE INVENTION

Figure 1:
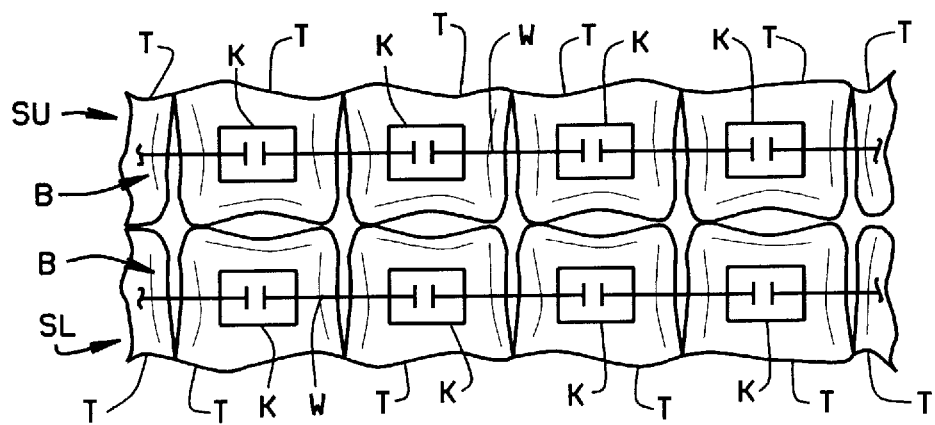
FIG. 1 is a representation of a patient's set of teeth to which brace are applied.
Figure 2:
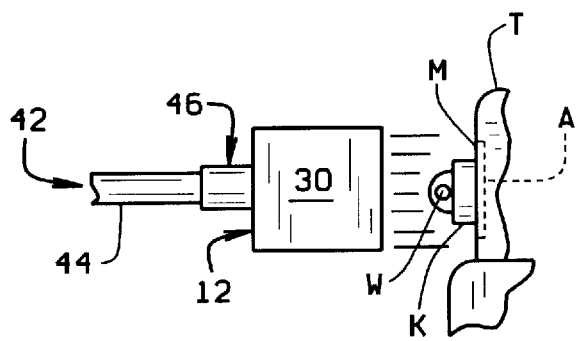
FIG. 2 is a side view of the tooth and illustrates positioning of a device of the present invention adjacent the teeth to direct light onto the tooth to attach a bracket to the tooth to support a brace.
Figure 3:
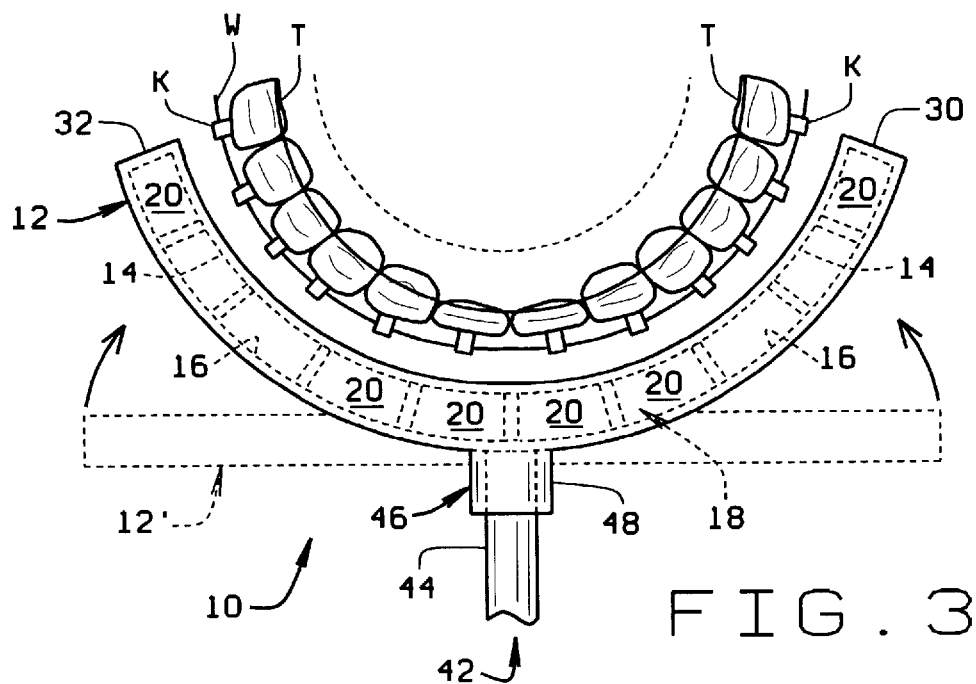
FIG. 3 is a plan view of a patient's mouth illustrating an arch shape of a patient's set of teeth and conformance of flexible housing of the device to the arch shape.

Referring to the drawings, a patient has teeth T to which braces are applied, or which may be treated to whiten the teeth. The patient has an upper set SU of teeth and a lower set SL of teeth. As shown in FIG. 3, the patient's teeth are generally in an arch shaped pattern conforming to the shape of the patient's upper and lower jaw, all as is well-known in the art. If the patient is to be fitted with braces B as shown in FIGS. 1–3, one set in the orthodontic procedure is to affix brackets K to each of the teeth in the upper or lower set of teeth for which the braces are applied. The type and construction of the brackets form no part of this invention; except, as shown in FIG. 2, an area A on the front of each tooth is cleaned and coated with a reactive chemical M. Thereafter, a bracket is set in place, and light from a light source is directed at the masked area. The light causes the chemical M to react and attach the bracket to the tooth; again, as is well-known in the art. This process is used for each tooth with the amount of time the light is directed at each tooth being for a predetermined period. Once all of the brackets have been attached to all of the teeth, a wire W is fitted into the brackets to complete installation of the brace. Because of the number of teeth involved, and the time interval required for light to be directed at each tooth, the light application of the process has heretofore taken a considerable amount of time. The same is true of a dental/orthodontic procedure in which light is directed at the teeth as part of a tooth whitening process.

A device 10 of the present invention is for use in performing one of the aforementioned orthodontic procedures. It is a primary feature of the invention that use of the device substantially shortens the amount of time light is directed at the teeth because the device allows the light to be simultaneously directed at the teeth in a set of teeth subjected to the procedure. The device first includes a pliable housing 12 which is deformable to conform to an arch shape of a set of the patient's teeth as particularly shown in FIG. 3. As viewed in the drawings, housing 12 is an elongate, flexible housing and is made of a lightweight rubber, plastic, glass, acrylic or thin metal/foil material. Because the housing is made of a flexible material, once it is formed into a particular arch shape, the housing will retain that shape during usage with a patient. The housing has a length at least corresponding to the arcuate length of the patient's set of teeth, and for this purpose, the housing is available in a number of different lengths for use with patients having different sized mouths. It will be understood that the set of teeth involved does not include all of the patient's upper or lower set of teeth, but only those upon which the procedure is being performed. In FIG. 3, the housing is indicated in outline form as 12' and represents an initial housing configuration in which the housing is generally straight from one end to the other. Then, prior to performing the procedure, an orthodontist or orthodontic assistant presses against the ends of the housing as indicated in the drawing so the resulting curvature of the housing (indicated 12 in FIG. 3) conforms to the arch shape of the set of teeth. Since it is typical for a mold to be made of the patient's teeth in preparation for the procedure, the curvature of the housing can be accomplished using the mold, thereby eliminating the need for additional office visits by the patient, and patient discomfort.

The housing has a front face or surface 14 which extends lengthwise of the housing. This face is positioned adjacent the patient's teeth during use of the device. The face is of a transparent, light transmissive material so light introduced into the housing, as described hereinafter, is transmitted through the housing and directed at the patient's teeth. A portion of the light striking the patient's teeth will be reflected back into the housing through the light transmissive material comprising front face 14. The housing has a rear face or surface 16. An interior portion of this face is of a light reflective material so light striking face 16 is reflected back toward the patient's teeth.

Further, device 10 includes light diffusion means indicated generally 18 installed in housing 12 for diffusing light directed into the housing throughout the housing. This can be accomplished by a variety of methods. In the simplest form, a light transmissive front face 14 and a light reflective face 16 provides a means of directing the light onto the patient's teeth. To achieve a controlled light intensity, the light transmissive front face 14 can have variable transmittance with lower transmittance near the center of the housing where the light is most intense. Alternative means of achieving controlled light distribution emitted from the front of the housing 12 include optical gratings 20 extending between upper and lower surfaces 22, 24 of the housing and leaky light guides. In both of these methods, light in housing 12 is allowed to escape by disturbing the light path. Gratings achieve this by a periodic surface relief whereas a leaky light guide achieves this through a reduction in the size of the guiding region. By varying the grating period and amplitude, gratings can be designed to achieve a variety of intensity distributions along housing 12. In a similar manner, the appropriate design of the guiding region in a leaky light guide will achieve a specified intensity distribution along housing 12. Furthermore, the light emitted by any of these means can be restricted to certain grates 20 thereby delivering the light to specific teeth. In addition, the interior surfaces 26, 28 respectively of the housing end walls are each also formed or lined with a light reflective material so light reaching one end of the housing is reflected back along the length of the housing toward its other end. The result of the light reflective and light transmissive surfaces, and the gratings and leaky light guides forming light diffusion means 18 is to diffuse light throughout the housing and simultaneously direct light of a uniform intensity at all of the patient's teeth on which the orthodontic process is being performed. As a result, it is no longer necessary to direct light first at one tooth and then at another thereby substantially reducing the amount of time required for light to be used in performing the process, while enhancing efficiency of the process.

Figure 4:
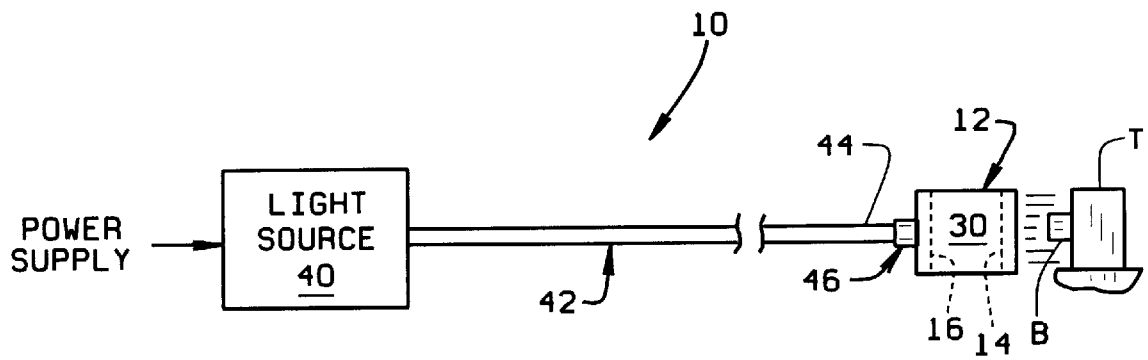
FIG. 4 is a simplified block diagram of the device.

In FIG. 4, a light source 40 is a conventional laser light source used in orthodontic procedures. A light transmissive cable 42 is preferably a conventional fiber optic cable also used in orthodontic procedures. Conventionally, a distal end 44 of the fiber optic cable is held adjacent a patient's tooth by the orthodontist or his or her assistant so light emitted from the end of the cable is directed at a tooth. Now, device 10 includes attachment means 46 for attaching housing 12 to end 44 of cable 42 for light transmitted through the cable to be directed into the housing. Means 46 includes an adaptor 48 which is of a hollow, cylindrical shape the inner diameter of which corresponds to the diameter of end 44 of cable 42 for the adaptor to fit onto the end of the cable. Adaptor 48 is located intermediate the ends of the housing, and preferably at the midpoint along the length of the housing. An aperture 50 is formed in rear surface 16 of the housing, the size of the aperture corresponding to the size of the distal end of the fiber optic cable captured in adaptor 48. Thus, light emitted from the end of cable 42 is directed into the housing through the aperture and dispersed throughout the housing as previously discussed.

Figure 5:
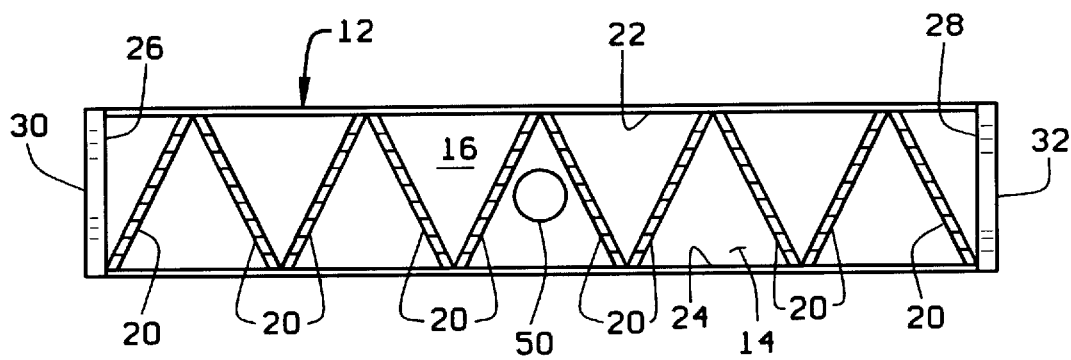
FIG. 5 is front elevational view of the housing.
Figure 6:
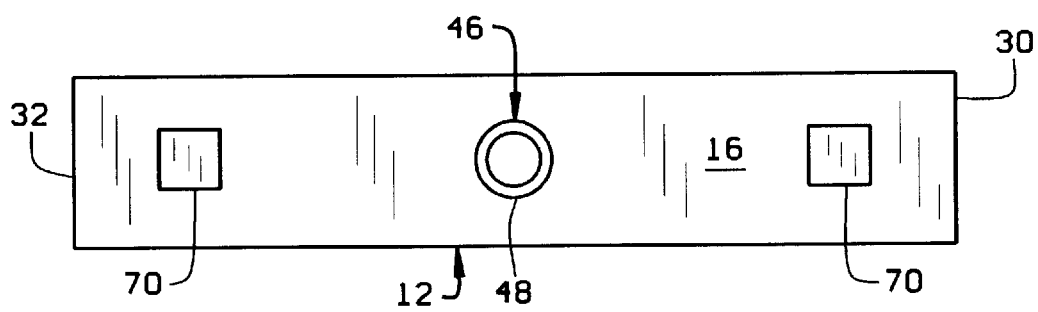
FIG. 6 is a rear elevational view of the housing.
Figure 7:
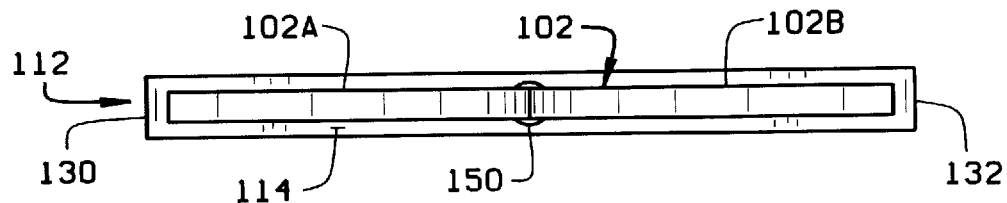
FIG. 7 is a front elevational view of a second embodiment of the housing.
Figure 8:
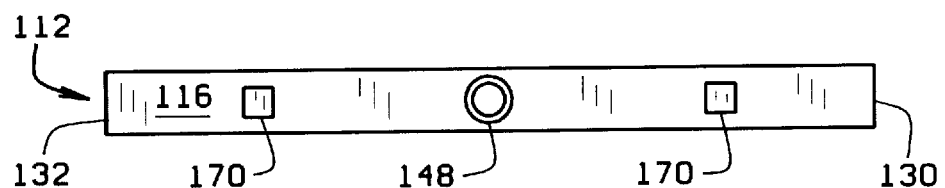
FIG. 8 is a rear elevational view thereof.

As shown in FIG. 5, end walls 30, 32 of housing 12, in addition to having the light reflective inner surfaces 26, 28, are also formed of a cushioning material (i.e. formable acrylic). Thus, when the device is in use, any contact between housing 12 and the inside of the patient's mouth or gums will not injure the mouth or gums. As shown in FIG. 6, a pair of pads 70 are attached to the outer face of rear surface 16 of the housing. These pads aid the user of the device in positioning the housing in the patient's mouth, and keeping it in place, without tearing or otherwise damaging the housing.

Referring to FIGS. 7–10 and 11–14, respective alternate embodiments of the invention are shown. In FIGS. 7–10 a support is indicated 112, and in FIGS. 11–14, a support is indicated 212. In each instance, the support is usable with the laser light source 40 and is connected to fiber optic cable 42 in the same manner as housing 10. Unlike the previously described embodiment, however, supports 112 and 212 support a fiber optic cable 102 or 202 respectively. Each support is made of a material similar to that of which housing 12 is made for the supports to be conformable to the arch shape of a patient's set of teeth in the same manner as housing 10. The pads 170 and 270 on the back of the support are used by the orthodontist or assistant in positioning the appliance adjacent the teeth and holding it there.

Figure 9:
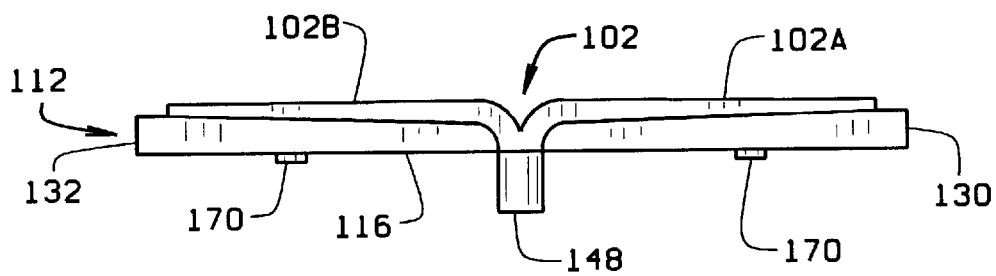
FIGS. 9 and 10 are respective top and bottom plan views of the housing.
Figure 10:
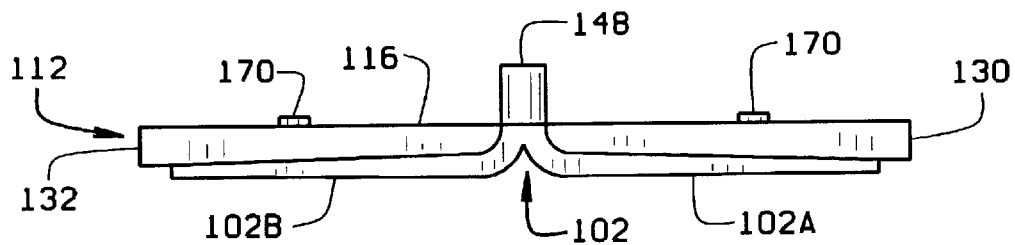
Figure 11:
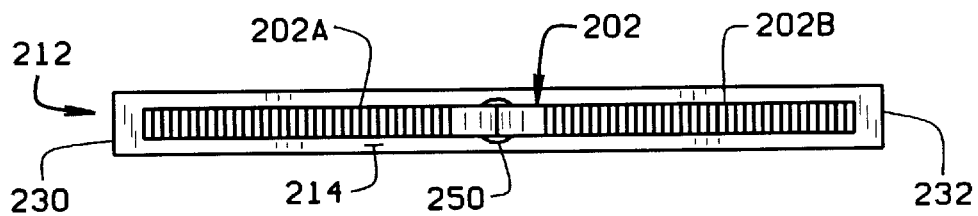
FIGS. 11 and 12 are views similar to FIGS. 7 and 8 for a third embodiment of the housing.
Figure 12:
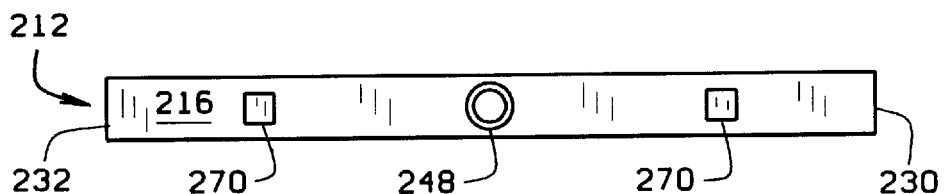
Figure 13:
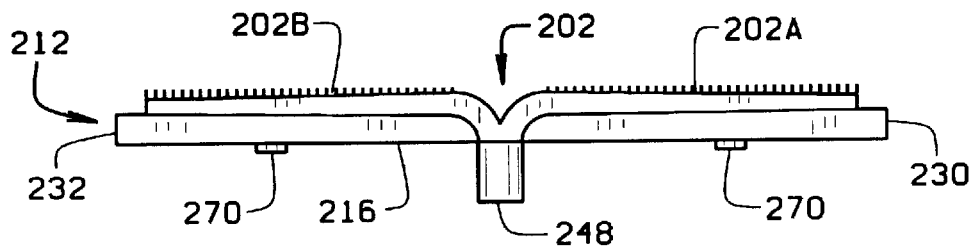
FIGS. 13 and 14 are respective top and bottom plan views of the third embodiment.
Figure 14:
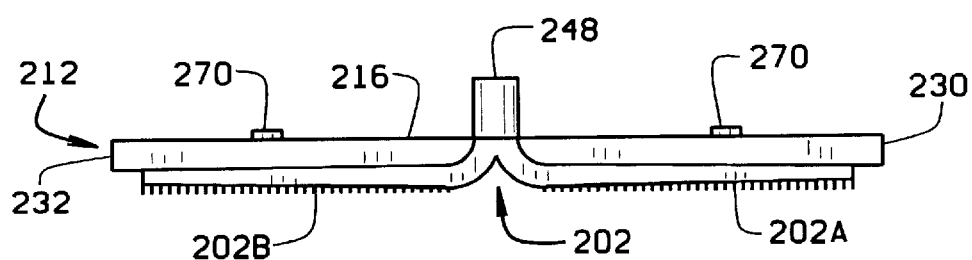

The optical cable 102 interfaces with the distal end of fiber optic cable 42 when adaptor 148 or 248 is fitted onto the end of cable 42. Fiber optic cable 102 or 202 each has respective sections 102A, 102B or 202A, 202B. One section of each cable extends from aperture 150 across a front face 114 or 214 of the support toward one side of the support; and, the other section of each cable extends from the aperture to the other side of the support. As shown in FIGS. 9 and 10, each of the sections 102A, 102B tapers from the aperture to the outer end of the support such that at the outer end of each cable section, no light is transmitted from the end of the cable. Rather, each section of cable is constructed to have spaced locations from which light transmitted through the section is directed at the patient's teeth. As a result, the same operative result is obtained using these support members as with housing 12.

What has been described is a device used by a dentist/orthodontist or the dentist's/orthodontist's technician or assistant to install brackets on teeth to which a brace is applied, or in teeth whitening processes. The amount of time light is applied to a patient's teeth using the device can be drastically reduced. The device readily attaches to an existing fiber optic cable used in these procedures and the device allows light to be simultaneously directed at all of the teeth in an upper or lower set of teeth involved in the process. The device is conformable to the arch shape of a person's set of teeth and this conformance can be done in advance of the person's treatment using a mold previously taken of the person's teeth. The device is available in various sizes so to accommodate people having different sized sets of teeth and the device is made of a soft, deformable material readily shaped to conform to the arch of a person's set of teeth. A light diffusion system employed by the device enables light from the end of a fiber optic cable to which the device is attached to be simultaneously diffused throughout the device and directed at all of the patient's teeth, the light being of uniform intensity. The device is easily attached and detached from the fiber optic cable to allow for autoclaving or for disposing. The device is low in cost enabling the dentist/orthodontist to purchase a new device per individual patent adhering to infection control standards and/or for limited autoclavable multiple use. Alternatively, a fiber optic cable and cable support (which are also deformable to conform to the arch shape of a patient's teeth) can be connected to the light transmissive cable to achieve the same result. Finally, it will be appreciated that while the above description has been presented with respect to humans on which orthodontic processes are performed, the device can also be effectively employed with animal patents as well on which an orthodontic process is performed.

In view of the foregoing, it will be seen that the several objects of the invention are achieved and other advantageous results are obtained.

As various changes could be made in the above constructions without departing from the scope of the invention, it is intended that all matter contained in the above description or shown in the accompanying drawings shall be interpreted as illustrative and not in a limiting sense.

I claim:

1. A device for use in performing an orthodontic process in which light supplied from a light source through a light transmissive cable is directed at a patient's teeth comprising:

a support deformable to conform to an arch shape of a set of the patient's teeth, the support having a length at least corresponding to the arcuate length of the set of teeth, said support comprising a housing formed of a flexible material which retains its shape once the housing is deformed to conform to the arch shape of said set of teeth;

attachment means attaching the support to an end of the cable for light transmitted through the cable to be directed into the support; and, light diffusion means diffusing light directed into the support throughout the support, for diffused light to be directed from the device simultaneously at all of the patient's teeth on which the orthodontic process is being pre-formed to substantially reduce the amount of time required for light to be used in performing the process.

2. The device of claim 1 wherein a cast is made of the patient's set of teeth and said housing shape can be made using said cast.

3. The device of claim 1 wherein said housing has a surface positioned adjacent the patient's set of teeth when the orthodontic process is being pre-formed, and said surface is formed of a light transmissive material for light to be directed through said surface at the patient's teeth.

4. The device of claim 3 wherein said housing further has a surface opposite said light transmissive surface, said opposite surface being formed of a light reflective material which reflects light toward said light transmissive surface.

5. The device of claim 4 wherein said light diffusion means includes means for diffusing light from one end of said housing to an opposite end thereof, said diffusion means directing light passing through said housing at said light transmissive and light reflective surfaces of said housing.

6. The device of claim 5 wherein said light diffusion means includes a series of light transmissive grates extending across said housing between said light transmissive and said light reflective surfaces.

7. The device of claim 6 wherein each of said grates extends between said light transmissive and light reflective surfaces at an angle other than an orthogonal angle.

8. The device of claim 6 wherein said ends of said housing are each lined with a light reflective material for light reaching one end of said housing being reflected back along the length of said housing toward the other end thereof.

9. The device of claim 1 wherein said light transmissive cable is a fiber optic cable and said attachment means includes an adaptor sized to fit over an end of said cable to connect said housing to said cable.

10. The device of claim 9 wherein said adaptor is mounted on said housing intermediate the ends of the housing.

11. The device of claim 10 wherein said adaptor is mounted to said light reflective surface of said housing, said housing having a wall on one face of which said light reflective surface is formed and said wall having an aperture therein by which light from the end of said fiber optic cable to which said housing is attached is directed into said housing.

12. The device of claim 11 further including means positioned at each end of said housing for cushioning said patient's mouth if said housing comes into contact with said mouth.

13. The device of claim 12 further including pad means on an outside surface of said wall for a user of said device to manipulate said housing when positioning said housing adjacent said teeth.

14. The device of claim 1 wherein said support includes means for supporting a light transmissive cable extending lengthwise of the device across a face of the device positioned adjacent said patient's teeth for light from said light source directed through said light transmissive cable to be transmitted into said light transmissive cable supported on said support so light can be simultaneously directed at all of said patient's teeth.

15. The device of claim 14 wherein said light transmissive cable supported on said support is a fiber optic cable.

16. The device of claim 15 wherein said fiber optic cable is a split cable in which one section of said cable extends across one portion of said face of said support and a second section of said cable extends across a second portion of said face.

17. A method of attaching brackets to a patient's teeth for installing braces on said teeth comprising:

forming a housing of a flexible material which retains its shape once the housing is deformed to conform to an arch shape of a set of the patient's teeth;

deforming said housing to conform to said arch shape of said set of teeth, the housing having a length at least corresponding to the arcuate length of said set of teeth;

attaching said housing to one end of a light transmissive cable the other end of which is connected to a source of light for light to be transmitted through the cable from said source into said housing; and, diffusing light directed into the housing throughout the housing, the housing having a light transmissive surface by which the diffused light is simultaneously directed at all of the patient's teeth to which brackets are being attached to effect attachment of all the brackets to the teeth at the same time and substantially reduce the amount of time light is directed at the patient's teeth in order to effect attachment of said brackets.

18. The method of claim 17 further including making a cast is of the patient's set of teeth and shaping said housing using said cast for said housing shape to be preformed prior to performing the method.

19. A method for whitening a patient's teeth, as well as other previously mentioned dental procedures, comprising:

deforming a housing to conform to an arch shape of a set of the patient's teeth, the housing having a length at least corresponding to the arcuate length of said set of teeth;

attaching said housing to one end of a light transmissive cable the other end of which is connected to a source of light for light to be transmitted through the cable from said source into said housing; and, diffusing light directed into the housing throughout the housing, the housing having a light transmissive surface by which the diffused light is simultaneously directed at all of the patient's teeth which are to be whitened or restored so to effect whitening/restoring of the patient's teeth while substantially reducing the amount of time light is directed at the patient's teeth in order to whiten and restore them.

20. The method of claim 19 further including forming the housing of a flexible material which retains its shape once the housing is deformed to conform to the arch shape of the patient's set of teeth.

21. The method of claim 20 further including making a cast of the patient's set of teeth and shaping said housing using said cast for said housing shape to be pre-formed prior to performing the method.

* * * * *